United States Patent

Carlsson et al.

[11] Patent Number: 5,154,612
[45] Date of Patent: Oct. 13, 1992

[54] CAP

[75] Inventors: Lennart Carlsson; Lars Jörnéus, both of Mölndal, Sweden

[73] Assignee: Nobelpharma AB, Gothenburg, Sweden

[21] Appl. No.: 641,866

[22] Filed: Jan. 16, 1991

[30] Foreign Application Priority Data

Jan. 18, 1990 [SE] Sweden .............................. 9000176

[51] Int. Cl.$^5$ .............................................. A61C 8/00
[52] U.S. Cl. .................................................... 433/173
[58] Field of Search .................. 433/173, 174, 175, 176

[56] References Cited

U.S. PATENT DOCUMENTS

| 3,827,145 | 8/1974 | Richards | 433/175 |
| 4,103,422 | 8/1978 | Weiss et al. | 433/174 |
| 4,547,157 | 10/1985 | Driskell | 433/173 |
| 4,758,161 | 7/1988 | Niznick | 433/173 |
| 4,790,753 | 12/1988 | Fradera | 433/174 |
| 4,824,372 | 4/1989 | Jorneus et al. | 433/174 |

FOREIGN PATENT DOCUMENTS 3110693 9/1982 Fed. Rep. of Germany .
459152 12/1989 Sweden .

Primary Examiner—Cary E. O'Connor
Attorney, Agent, or Firm—Pollock, Vande Sande & Priddy

[57] ABSTRACT

A device made of a tissue-compatible material is intended to temporarily cover a spacer of a dental implant during a period of incorporation of the dental implant, preferably in a single-tooth replacement. The base section of the device is designed in such a way that it guides the healing of the mucous membrane to assume a contour such that securing of the final crown is facilitated, and a certain possibility of controlling the seam between the final crown and the spacer is afforded. The device is preferably made of an elastic material for good clamp fitting on the spacer, as a result of which the use of paste, dental cement or the like is eliminated.

5 Claims, 1 Drawing Sheet

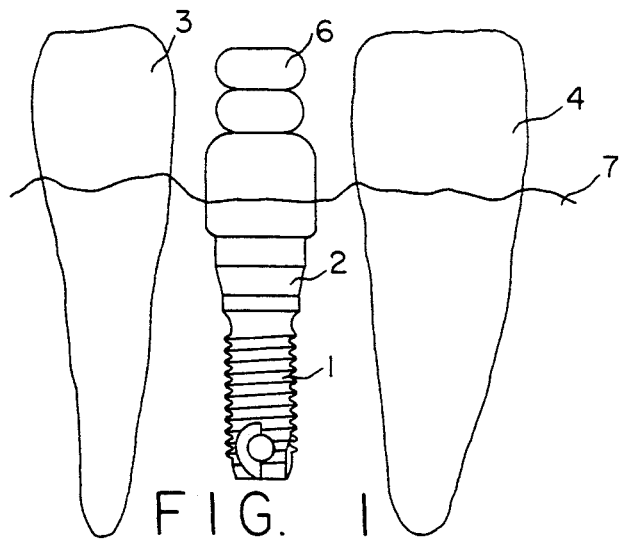
FIG. 1
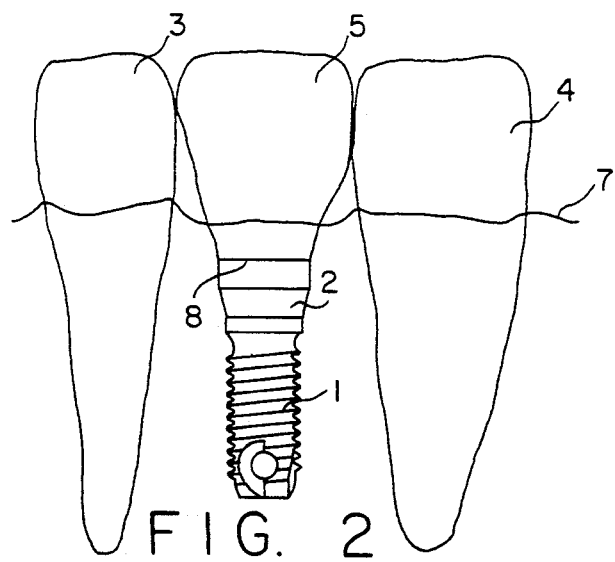
FIG. 2
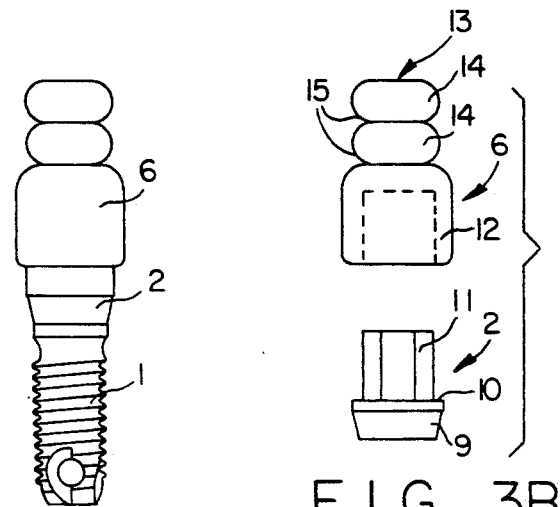
FIG. 3A
FIG. 3B

CAP

FIELD OF THE INVENTION

The present invention relates to a device made of a tissue-compatible material and intended to temporarily cover the so-called spacer during a particular period of incorporation of a dental implant, preferably in a single-tooth replacement.

BACKGROUND OF THE INVENTION

It is already known to permanently anchor a dental prosthesis in the jaw with the aid of titanium screws implanted in the jawbone. The screws are anchored in holes in the bone in such a way that the upper part of the screw is located levelled with or immediately below the top surface of the jawbone The screw is then covered over with a flap of mucous membrane and is left unloaded for a rest period of 3 to 6 months so that the bone can grow securely to and form a unit with the implanted screw. After the rest period the screw is exposed and a spacer element, preferably also made of titanium, is screwed into place, after which a dental prosthesis is anchored on the spacer element. The dental prosthesis must in this case be adapted accurately to the actual appearance of the jaw with the implanted titanium elements.

Swedish Patent 8701949-3 describes a device for anchoring a so-called single-tooth replacement on an implanted titanium element. In this case the spacer element consists of a spacer sleeve which is anchored on the titanium element with a special spacer screw which is provided with an externally threaded section which engages in a threaded bore in the upper part of the titanium element.

Swedish Design Application 892064 shows another type of spacer element with a conically designed base part which connects to the upper part of the titanium element and an upper, hexagonally designed column part, the whole component being made of titanium.

The base part of the titanium spacer can be designed in different lengths In this case a length is chosen which is such that the shoulder of the base part ends 1 to 3 mm under the surface of the gum, so that no titanium is visible after the crown has been cemented in place. The crown is designed so that it extends down to the shoulder of the spacer.

Before the crown is fitted, a certain period of incorporation is required in order for the gum swelling to go down. In addition, a certain time is needed in order to produce the final crown, since the latter must be manufactured individually for each patient.

During this period, when the manufacture of the crown and the incorporation take place, the gum must be kept away from the shoulder and the column part of the spacer. It is also important to shape the gum so that the crown, which in most cases is wider than the base section of the spacer, can be secured easily in place.

It is also advantageous if the pocket in the gum is slightly larger than the final crown. This in fact gives the dentist an opportunity to control the so-called cement seam which is produced when the crown is cemented or glued into place, for example using normal dental cement.

The mucous membrane normally contracts quickly around the crown when it has been fitted. Therefore it does not matter if the pocket in the gum is so large that space for clearing excess cement has been left after the cap has been removed.

Caps are previously known which are secured by means of a screw and whose main task is to protect the thread in which they are screwed tight. These previously known caps cannot however be used on the spacer elements which have been described above, since both the spacer and the screw holding the spacer in place have no internal thread. Adhesive or so-called temporary cement should not be used either, since it may be difficult to remove the cap and, if it has been successfully removed, there will still be laborious work involved in clearing away adhesive and cement residues.

Nor have these previously known caps been designed in such a way that a pocket has been formed in the mucous membrane, which pocket facilitates securing of the crown and inspection of the seam between the crown and the spacer.

SUMMARY OF THE INVENTION

An object of this invention is to provide a device (cap) which can also be used for the above type of spacer element which does not have an internal thread.

Another object of the invention is to provide a device (cap) which guides the healing of the mucous membrane more effectively than known devices in such a way that the mucous membrane acquires a contour facilitating securing of the crown, and which also affords a certain possibility of controlling the cement seam between the crown and the spacer element.

A further object of the invention is to provide a cap which affords improved support for a temporary crown during the incorporation period before the permanent crown is applied.

According to present invention, the base part of the cap is designed in such a way that it guides the healing of the mucous membrane to assume a contour which would facilitate securing of the crown, and which also affords a certain possibility of controlling the seam between the crown and the spacer.

The cap is preferably made of an elastic material so that good clamp fitting on the spacer is obtained. This eliminates the use of paste, dental cement or the like.

In one advantageous embodiment, the upper part of the cap is moreover provided with retention elements for affording positive locking between the device and a temporarily applied crown.

BRIEF DESCRIPTION OF THE DRAWINGS

One preferred embodiment of the present invention will be described in greater detail below with reference to the attached drawing in which FIG. 1 shows a dental implant with a cap according to the invention, FIG. 2 shows the implant with a crown fitted (single-tooth replacement), and FIGS. 3A and 3B show separately the cap and the spacer element of the implant with which the cap cooperates.

DETAILED DESCRIPTION OF THE PREFERRED EMBODIMENT

FIG. 1 shows a dental implant for a single-tooth replacement, which comprises a titanium screw 1 and a spacer element 2 also made of titanium. The implant is arranged between two natural teeth 3, 4, and the intention is for a crown 5 to be applied on the spacer element by means of cementing in the manner described in the introduction.

FIG. 1 shows how a cap 6 is temporarily arranged on the spacer element 2 during the incorporation period of about 14 days during which the gum swelling will go down and the final crown 5 is manufactured. The base part of the cap is wider than the base part of the spacer in order to hold the gum away from the shoulder of the spacer element, and so that a pocket is formed in the gum, which is slightly larger than the final crown. As can be seen from the figure, the base part of the cap, extends down some distance into the edge 7 of the mucous membrane (gum).

It can be seen from FIG. 2 that the so-called cement seam 8, which occurs between the crown and the shoulder of the spacer element, is situated below the surface 7 of the mucous membrane and that it is therefore advantageous if the pocket which is formed by the cap is slightly larger than the final crown, in order to give the dentist the possibility of controlling the seam after cementing.

FIG. 3 shows a spacer element 2 which is known and which has a base part 9, in different lengths, a shoulder 10 and a hexagonal column part 11. The cap 6 is made of an elastic material so that good clamp fitting on the spacer is obtained, as a result of which the use of cement or adhesive is eliminated. The base section 12 of the cap is thick-walled in order to keep the mucous membrane sufficiently away.

The upper part 13 of the cap is designed in such a way that a temporary crown acquires good retention as a result of positive locking between the fixing compound which fills the space between the temporary crown and the cap. The upper part 13 is therefore made long so that it provides support for the temporary crown, and it is provided with a number of retention elements 14 (two in the figure) for positive locking.

Since the temporary crowns are of different sizes internally, it must be possible for the length of the cap to be easily adapted. This is achieved by the cap being cut off at the special notches 15 between the retention knobs.

In some cases the retention element can be completely removed, especially when no temporary crown is to be secured on the cap, and instead the latter is to be as small as possible.

We claim:

1. A device made of a tissue-compatible material and intended to temporarily cover a spacer of a dental implant during a period of incorporation of said dental implant and to support a temporary dental crown, said device comprising:
   a cup-shaped base portion having its outer wall which is wider than a base section of a final crown and has a length which extends a predetermined distance below the edge of the mucous membrane such as to guide the healing of the mucous membrane during the incorporation period for forming a pocket in the mucous membrane which facilitates securing of the final dental crown and allows for controlling of a seam between the final dental crown and said spacer, and
   an upper portion extending upwardly from said base portion for supporting said temporary dental crown during the healing period, and wherein at least said cup-shaped portion is made of an elastic material such that upon insertion of said device onto said spacer a clamp fitting is obtained between said cup shaped portion and said spacer.

2. A device according to claim 1, wherein said upper portion is provided with retention elements for allowing positive locking between said device and said temporary dental crown.

3. A device according to claim 2, wherein said upper portion also includes break notches for facilitating shortening of the length of said upper portion.

4. A device according to claim 2, wherein said retention elements include a plurality of retention knobs made of an elastic material.

5. A device according to claim 3, wherein said retention elements include a plurality of retention knobs made of an elastic material.

* * * * *